United States Patent [19]

Grollier et al.

[11] Patent Number: 4,668,236

[45] Date of Patent: May 26, 1987

[54] DYEING COMPOSITION FOR KERATINOUS FIBRES CONTAINING AT LEAST ONE CO-SOLUBILIZED N-SUBSTITUTED 2-NITRO-PARA-PHENYLENEDIAMINE AND CORRESPONDING PROCESSES FOR DYEING KERATINOUS FIBRES

[75] Inventors: Jean-François Grollier, Paris; Jean Cotteret, Franconville; Georges Rosenbaum, Asnieres, all of France

[73] Assignee: L'Oreal, Paris, France

[21] Appl. No.: 744,679

[22] Filed: Jun. 14, 1985

[30] Foreign Application Priority Data

Jun. 20, 1984 [LU] Luxembourg ............................ 85421

[51] Int. Cl.$^4$ ................................................. A61K 7/13
[52] U.S. Cl. ............................................ 8/405; 8/410; 8/415; 8/425; 8/428; 8/435
[58] Field of Search .................... 8/405, 410, 415, 425, 8/428, 435

[56] References Cited

U.S. PATENT DOCUMENTS 3,168,442 2/1965 Brunner et al. ............................ 8/415
4,170,229 10/1979 Olson .................................. 514/390

FOREIGN PATENT DOCUMENTS 744438 2/1956 United Kingdom ..................... 8/405
1213697 11/1970 United Kingdom ..................... 8/406
1219035 1/1971 United Kingdom ..................... 8/409

OTHER PUBLICATIONS

Chemical Abstracts, 89: 168942v (1978).

Primary Examiner—Albert T. Meyers
Assistant Examiner—John M. Kilcoyne
Attorney, Agent, or Firm—Cushman, Darby & Cushman

[57] ABSTRACT

The invention relates to a dyeing composition for keratinous fibres containing, in a suitable vehicle, at least one nitrated direct dye of the 2-nitro-paraphenylenediamine series, in which the amino group in position 4 is mono- or disubstituted with lower alkyl or hydroxyalkyl radicals and in which the amino group in position 1 is optionally monosubstituted with a lower alkyl or hydroxyalkyl radial, and the aromatic ring can be substituted or unsubstituted on the remaining positions; the invention consists in introducing into such a composition an imidazolidinedione or one of its substitution derivatives, to improve the solubility of the abovementioned nitrated direct dye by a co-solubilization phenomenon. The invention also relates to a process for dyeing keratinous fibres using such compositions.

9 Claims, No Drawings

DYEING COMPOSITION FOR KERATINOUS FIBRES CONTAINING AT LEAST ONE CO-SOLUBILIZED N-SUBSTITUTED 2-NITRO-PARA-PHENYLENEDIAMINE AND CORRESPONDING PROCESSES FOR DYEING KERATINOUS FIBRES

The present invention relates to a dyeing composition for keratinous fibres, and especially for living human hair, containing at least one nitrated direct dye of the N-substituted 2-nitro-para-phenylenediamine series. The invention also relates to a dyeing process using the said compositions.

It is known to use nitro-para-phenylenediamines and their substitution products in the composition of dyeing solutions for dyeing keratinous fibres.

These dyes endow the hair with a direct coloration also known as semi-permanent, and they can also be used in oxidation dyeing compositions to obtain, with the oxidation dyes, complementary highlights and shades rich in highlights.

In hair dyeing, blue, red, mauve and violet tints are necessary as components for achieving the desired tints, and it has already been proposed to use, as direct hair dyes of this type, 2-nitro-para-phenylenediamine derivatives in which the amino group in position 4 is mono- or disubstituted. The amino group in position 1 can, for its part, be monosubstituted and the aromatic ring can be either substituted or unsubstituted on the remaining positions.

These classical 2-nitro-para-phenylenediamine derivatives are more often than not insufficiently soluble or dispersible in water, and this constitutes a major disadvantage in hair dyeing for achieving dark shades; if the dye is not solubilized in the dyeing medium, this leads to irregularities in dyeing, with a great risk of obtaining weaker coloring than that envisaged. In fact, in the particular case of dyeing formulations rich in dyes for obtaining varied shades, or in the case of poorly solubilized media, it happens that the dyes recrystallize, remain in the dye bath and do not pass onto the hair.

Dyeing preparations produced from 2-nitro-para-phenylenediamine derivatives in which the amino group in position 4 is mono- or disubstituted and in which the amino group in position 1 can optionally be monosubstituted, the aromatic ring being able to be substituted or unsubstituted on the remaining positions, have consequently not hitherto completely satisfied the demands of good dyeing.

Quite surprisingly, we have discovered, that, by introducing an imidazolidinedione, or one of its substitution derivatives, into a dyeing composition containing at least one red, mauve, blue or violet nitrated direct dye consisting of a 2-nitro-para-phenylenediamine in which the amino group in position 4 is mono- or disubstituted with lower alkyl or hydroxyalkyl radicals and in which the amino group in position 1 is optionally monosubstituted with a lower alkyl or hydroxyalkyl radical, the aromatic ring being able to be substituted or unsubstituted on the remaining positions, the solubility of the red, mauve, blue or violet nitrated direct dye or dyes was improved by co-solubilization.

The dyeing compositions according to the invention have the advantage of making better use of the potential dyeing capacity of the nitrated direct dye of the substituted 2-nitro-para-phenylenediamine series as mentioned above.

In effect, the co-solubilization agent introduced makes it possible to greatly reduce the risks of recrystallization of the nitrated direct dyes of the 2-nitro-para-phenylenediamine series in dyeing formulations rich in these dyes or in dyeing formulations having a poorly solubilizing medium. The co-solubilization agent used in the composition according to the invention also has the advantage of being colorless, and consequently of not modifying in any way the shades initially desired, which result from the combination of several dyes of different colors.

The present invention provides a composition suitable for dyeing keratinous fibres and, more especially, human hair, comprising, in a suitable vehicle, at least one nitrated direct dye of the formula (I):

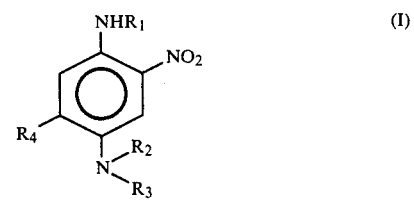

in which:
  $R_1$ is hydrogen, alkyl of 1 of 2 carbon atoms or hydroxyethyl;
  $R_2$ is hydroxyethyl;
  $R_3$ is hydrogen, alkyl of 1 or 2 carbon atoms or hydroxyethyl; each amino group being in free or salified form;
  $R_4$ is hydrogen, alkyl of from 1 to 4 carbon atoms or a halogen, with the proviso that, when $R_4$ is not hydrogen, $R_3$ is hydrogen;
and at least one imidazolidinedione, or derivative thereof, of formula (II):

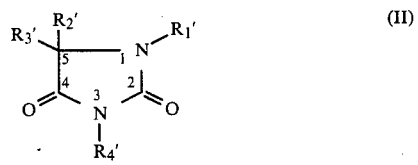

in which formula:
  $R_1'$ and $R_4'$ which may be the same or different are each hydrogen or alkyl of one or two carbon atoms;
  $R_2'$ is hydrogen, alkyl of 1 or 2 carbon atoms or an aromatic group eg. an aromatic hydrocarbon such as phenyl or phenanthryl;
  $R_3'$ is hydrogen, alkyl of 1 or 2 carbon atoms, an aromatic hydrocarbon group, ureido or carboxymethyl group;
or acid salt thereof.

Compounds of this type which are more especially preferred in the composition are:
  (a) the compound of formula (II) for which $R_1' = R_2' = R_4' = H$ and $R_3' =$ ureido, namely allantoin;
  (b) the compound of formula (II) for which $R_1' = R_4' = H$, $R_2' =$ methyl and $R_3' =$ phenyl, namely 5-methyl-5-phenylhydantoin.

The compounds of formula (I), the solubility of which can be increased as a result of the presence of at least one compound of formula (II), are, in particular, those for which:

(a) $R_1$=methyl, $R_2=R_3=\beta$—hydroxyethyl, $R_4$=H;
(b) $R_1=R_3$=methyl, $R_2=\beta$—hydroxyethyl and $R_4$=H;
(c) $R_1=R_2=R_3=\beta$—hydroxyethyl and $R_4$=H;
(d) $R_1=R_3$=H, $R_2=\beta$—hydroxyethyl and $R_4$=methyl as well as the corresponding acid salts.

By way of explanation, the solubility limits at 18° C. of the dyes of formula (I) listed above in the presence of a fixed amount or product of formula (II) have been collated in the table which follows, these solubility limits being measured in the following composition:

| Product of formula (II) | y g |
|---|---|
| Dye of formula (I) | x g |
| Ethylene glycol monoethyl ether | 10 g |
| 2-Amino-2-methyl-1-propanol qs | pH 9.6 |
| Water qs | 100 g | x is the maximum amount of the dye in question of formula (I) which can be dissolved in the particular medium thus defined. To determine the solubilities, the procedure is as follows:

A large excess of dye of formula (I) is dispersed with y g of product of formula (II) in the cosmetic base described above. The composition is left for 15 minutes at 60° C. (water bath) and then cooled with the ambient air with stirring for 30 minutes (checking that the ambient temperature is greater than 18° C.). After these 30 minutes, the composition is introduced into a chamber maintained at 18° C. The composition must remain there for at least 48 hours. After its removal from the chamber, the composition is immediately filtered. The collected filtrates are then analyzed by high performance liquid chromatography (HPLC) to determine the dye content.

| Dye of formula (I) | Solubility limits of the dye of formula (I) | | |
|---|---|---|---|
| | Alone y = 0 | Combined with allantoin y = 1.5 g | Combined with 5-methyl-5-phenylhydantoin y = 0.5 g |
| 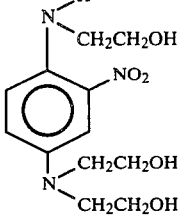 | 0.32% | 0.40% (1.25)* | |
| 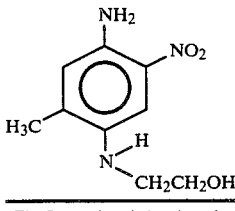 | 0.07% | 0.10% (1.43)* | |

| Dye of formula (I) | Solubility limits of the dye of formula (I) | | |
|---|---|---|---|
| | Alone y = 0 | Combined with allantoin y = 1.5 g | Combined with 5-methyl-5-phenylhydantoin y = 0.5 g |
| 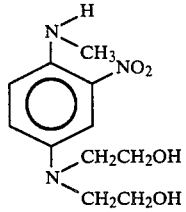 | 0.74% | 1.06% (1.43)* | 1.08% (1.46)* |
| 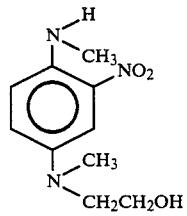 | 0.07% | 0.08% (1.14)* | 0.09% (1.29)* |

*The figure given in brackets shows the improvement in the solubility of the dye of formula (I) in the presence of a compound of formula (II). Thus, the dye of formula (I) given first is 1.25 times more soluble in the aforementioned medium when the amount of allantoin in the said medium increases from 0 to 1.5 g.

Particular compounds of formula (I) are described in French Pat. Nos. 1,101,904, 1,411,124, 1,454,313 and 1,454,314, as well as in U.S. Pat. No. 3,168,442 and in French Patent Application No. 2,492,370.

The compounds of formula (II) are well known to those versed in the art.

According to preferred embodiments, the compound or compounds of formula (I) (and/or the corresponding salts) is/are present in the dyeing composition according to the present invention at a concentration of from 0.05% to 5% by weight, and especially from 0.1 to 3% by weight, expressed as free base, relative to the total weight of the composition; the compound or compounds of formula (II) (and/or the corresponding salts) is/are present in the composition at a concentration of from 0.1% to 5% by weight, and preferably from 0.3% to 3% by weight, expressed as free base, relative to the total weight of the composition.

The compositions can contain, in addition to the compounds of formulae (I) and (II), in free or salified form:

(1) oxidation bases such as para-phenylenediamines, para-aminophenols are heterocyclic bases;

(2) one or more couplers belonging to the class of meta-phenylenediamines, meta-aminophenols or metadiphenols, or to the heterocyclic couplers, when the composition contains at least one oxidation base;

(3) ortho-phenylenediamines and ortho-aminophenols, optionally containing substituents on the ring or on the amino groups, or alternatively ortho-diphenol;

(4) dye precursors of the benzene series, containing on the ring at least three substituents chosen from the group consisting of hydroxy, methoxy or amino groups;

(5) dye precursors of the naphthalene series;

(6) leuco derivatives of indoanilines, indophenols or indoamines;

(7) nitrated direct dyes different from those of formula (I);

(8) non-nitrated direct dyes such as, for example, azo dyes, or anthraquinone dyes.

The compositions can contain, as a suitable vehicle, water and/or organic solvents which are acceptable from the cosmetic standpoint and, more especially, alcohols such as ethyl alcohol, isopropyl alcohol, benzyl alcohol and phenylethyl alcohol, or glycols or glycol ethers such as, for example, ethylene glycol and its monomethyl, monoethyl and monobutyl ethers, propylene glycol, butylene glycol and dipropylene glycol, as well as alkyl ethers of diethylene glycol, such as, for example, diethylene glycol monoethyl ether and monobutyl ether, at concentrations of from 0.5 to 20%, and preferably from 2 to 10%, by weight relative to the total weight of the composition.

There can also be added to the composition fatty amides, such as the mono- and diethanolamides of acids derived from coconut, lauric acid or oleic acid, at concentrations of from 0.05 to 10% by weight.

Anionic, cationic, nonionic or amphoteric surfactants, or mixtures thereof, can also be added to the composition. The surfactants are preferably present in the composition in a proportion from 0.1 to 50% by weight, and advantageously from 1 to 20% by weight, relative to the total weight of the composition.

Among surfactants, there may be mentioned more especially anionic surfactants used alone or mixed such as, in particular, alkali metal salts, magnesium salts, ammonium salts, amine salts or alkanolamine salts of the following compounds:

alkyl sulphates, alkyl ether sulphates, ethoxylated or non-ethoxylated alkylamide sulphates, alkyl sulphonates, alkylamide sulphonates, α-olefin sulphonates;
alkyl sulphoacetates; the alkyl radicals of these compounds having a linear chain of 12 to 18 carbon atoms.

It is also possible to use, in the form of salts mentioned above, fatty acids such as lauric, myristic, oleic, ricinoleic, palmitic or stearic acids, coconut oil or hydrogenated coconut oil acids, or carboxylic acids of polyglycol ethers.

By way of cationic surfactants, there may be mentioned more especially fatty amine salts, quaternary ammonium salts such as alkyldimethylbenzylammonium, alkyldimethylammonium, alkyldimethylhydroxyethylammonium and dimethyldialkylammonium chlorides and bromides, alkylpyridinium salts and imidazoline derivatives. The alkyl groups of the abovementioned quaternary ammonium derivatives are long-chain groups preferably having from 12 to 18 carbon atoms.

There may also be mentioned amine oxides among these compounds of a cationic nature.

Among amphoteric surfactants which can be used, there may be mentioned in particular alkylaminomono- and -dipropionates, betaines such as alkylbetaines, N-alkylsulphobetaines and N-alkylaminobetaines, the alkyl radical having from 1 to 22 carbon atoms, and cycloimidinium compounds such as alkylimidazolines.

Among nonionic surfactants which can optionally be used in the compositions, there may be mentioned condensation products of a mono-alcohol, alkylphenol, amide or α-diol with glycidol, such as the compounds described in French Pat. Nos. 2,091,516, 2,169,787 and 2,328,763; the compounds of formula:

$$RO-[C_2H_3O-(CH_2OH)]_m-H$$

in which R denotes an alkyl, alkenyl or alkylaryl radical having 8 to 22 carbon atoms, m being an integer from 1 to 10; polyethoxylated or polyglycerolated alcohols, alkylphenols or fatty acids having a $C_8$ to $C_{18}$ linear fatty chain; condensates of ethylene oxide and propylene oxide with fatty alcohols; polyethoxylated fatty amides containing at least 5 moles of ethylene oxide; and polyethoxylated fatty amines.

The thickening products which can be added to the composition are advantageously taken from the group formed by sodium alginate, gum arabic, guar gum, cellulose derivatives such as methylcellulose, hydroxyethylcellulose, hydroxypropylmethylcellulose, the sodium salt of carboxymethylcellulose and acrylic acid polymers.

Inorganic thickening agents such as bentonite can also be used. These thickeners may be used alone or mixed, and are preferably present in a proportion from 0.5 to 5% by weight relative to the total weight of the composition, and advantageously from 0.5 to 3% by weight.

The dyeing compositions can be formulated at acid, neutral or alkaline pH, and the pH can vary generally from 4 to 10.5, and preferably from 6 to 10. Among the alkalization agents which can be used, there may be mentioned alkanolamines and alkali metal or ammonium hydroxides and carbonates. Among acidification agents which can be used, there may be mentioned lactic acid, acetic acid, tartaric acid, phosphoric acid, hydrochloric acid and citric acid.

The dyeing compositions can contain, in addition, various conventional adjuvants such as antioxidants, perfumes, sequestering agents, film-forming products and treatment agents, dispersants, hair conditioning agents, preservatives and opacifiers, as well as any other adjuvants customarily used in cosmetics.

The dyeing compositions can take the various conventional forms, for hair dyeing, such as thickened or jellified liquids, creams or aerosol foams, or any other forms suitable for carrying out dyeing of keratinous fibres.

When it contains at least one oxidation base, the dyeing composition is mixed, at the time of use, with oxidizing agents such as peroxides and alkali metal persalts such as hydrogen peroxide, sodium peroxide, potassium peroxide, sodium perborate, sodium percarbonate and urea peroxide.

The present invention also relates to a new process for dyeing keratinous fibres, and especially human hair, in which the dyeing composition defined above is left to act on the keratinous fibres which are generally dry or damp. The compositions can be used as non-rinsed lotions when the compositions do not contain an oxidation dye, that is to say the compositions are applied to the keratinous fibres and these are then dried without intermediate rinsing. In the other modes of use, the dyeing compositions are applied to the keratinous fibres for an exposure time varying from 3 to 60 minutes, preferably from 5 to 45 minutes, and these are then rinsed, optionally washed, rinsed again and dried.

The dyeing compositions can be applied to natural or dyed hair which has been permanently waved or otherwise, or to strongly or lightly bleached hair, optionally permanently waved.

To enable the subject of the invention to be more fully understood, several modes of use will now be described by way of purely illustrative and non-limitative examples.

EXAMPLE 1

A cream having the following formulation is prepared:

| | |
|---|---|
| 1,4-Diaminobenzene | 0.15 g |
| 1,3-Dihydroxybenzene | 0.10 g |
| 2-Hydroxy-4-(β-hydroxyethyl)amino-1-methylbenzene | 0.05 g |
| 2-Amino-4-methyl-5-(β-hydroxyethyl)amino-1-nitrobenzene | 0.10 g |
| Allantoin | 2 g |
| Cetyl and stearyl alcohols in a 50:50 mixture | 18 g |
| 2-Octyldodecanol | 3 g |
| Cetyl/stearyl alcohol treated with 15 moles of ethylene oxide | 3 g |
| Ammonium lauryl sulphate | 12 g |
| Sodium bisulphite (35° Be) | 2 g |
| Ammonia solution (22° Be) | 10 g |
| Demineralized water qs | 100 g |

This cream is diluted at the time of use with 1.5 times its weight of "20 volumes" hydrogen peroxide. After the mixing, a cream is obtained which is applied for 30 minutes to dark blond hair.

After the hair has been rinsed, shampooed and dried, a coppery auburn blond coloration is obtained.

EXAMPLE 2

The following composition is prepared:

| | |
|---|---|
| 1-(β-Hydroxyethyl)amino-2-nitro-4-bis(β-hydroxyethyl)aminobenzene | 1.6 g |
| 3-Methylamino-4-nitrophenyl β,γ-dihydroxypropyl ether | 0.35 g |
| 2-(β-Hydroxyethyl)amino-1-nitrobenzene | 0.35 g |
| 2-Amino-3-methyl-1-nitrobenzene | 0.15 g |
| 1-(β-Hydroxyethyl)amino-2-nitro-4-aminobenzene | 0.3 g |
| 4-(-Hydroxyethyl)amino-3-nitrophenyl β,γ-dihydroxypropyl ether | 0.2 g |
| Allantoin | 2.5 g |
| 5-Methyl-5-phenylhydantoin | 0.4 g |
| Lauric diethanolamide | 2.5 g |
| Lauric acid | 1.5 g |
| 2-Ethoxyethanol | 6 g |
| Hydroxyethylcellulose sold under the name "NATROSOL 250 HHR" by "HERCULES" | 0.25 g |
| 2-Amino-2-methyl-1-propanol | 9.5 g |
| Demineralized water qs | 100 g |

This composition is applied for 20 minutes to dark chestnut-colored hair.

After the hair has been rinsed and dried, a deep tan coloration is obtained.

EXAMPLE 3

The following composition is prepared:

| | |
|---|---|
| 1-Methylamino-2-nitro-4-bis(β-hydroxyethyl)aminobenzene | 1.25 g |
| 2,5-Diamino-1-nitrobenzene | 0.4 g |
| 1-Amino-2-nitro-5-methyl-4-(β,γ-dihydroxypropyl)aminobenzene | 0.45 g |
| 1-(β-Hydroxyethyl)amino-2-(β-hydroxyethyl)amino-4-nitrobenzene | 0.1 g |
| 5-Methyl-5-phenylhydantoin | 0.5 g |
| Sodium lauryl ether sulphate (30% strength) | 20 g |
| Lauric diethanolamide | 4 g |

This composition is applied for 25 minutes to chestnut-colored hair.

After the hair has been rinsed and dried, a purple-violet auburn coloration is obtained.

It is obvious that the examples described above are in no way limitative and might give rise to any desirable modifications without thereby departing from the scope of the invention.

We claim:

1. A hair dye composition comprising a solution of, in a cosmetically acceptable solvent, (a) a direct dye of the formula

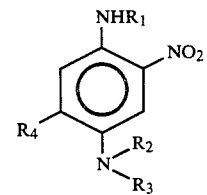

wherein
R$_1$ is selected from the group consisting of hydrogen, alkyl containing 1–2 carbon atoms and hydroxyethyl,
R$_2$ is hydroxyethyl,
R$_3$ is selected from the group consisting of hydrogen, alkyl containing 1–2 carbon atoms and hydroxyethyl,
R$_4$ is selected from the group consisting of hydrogen, alkyl containing 1–4 carbon atoms and halogen,
with the proviso that when R$_4$ is not hydrogen, R$_3$ is hydrogen, said direct dye being present in an amount ranging from 0.05 to 5 percent by weight based on the total weight of said composition, and (b) as a co-solubilization agent for the said direct dye defined in (a) above so as to reduce the risks of recrystallization of said direct dye in said cosmetically acceptable solvent, an imidazolidinedione of the formula

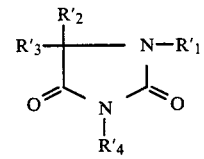

wherein
R$'_1$ and R$'_4$ each independently are selected from the group consisting of hydrogen and alkyl containing 1–2 carbon atoms,
R$'_2$ is selected from the group consisting of hydrogen, alkyl containing 1–2 carbon atoms, phenyl and phenanthryl,
R$'_3$ is selected from the group consisting of hydrogen, alkyl containing 1–2 carbon atoms, phenyl, ureido and carboxy methyl,
said imidazolidinedione being present in an amount ranging from 0.1 to 5 percent by weight based on the total weight of said composition.

2. The hair dye composition of claim 1 wherein said imidazolidinedione is allantoin or 5-methyl-5-phenylhydantoin.

3. The hair dye composition of claim 1 wherein said direct dye is selected from the group consisting of
    (a) a direct dye wherein $R_1$=methyl, $R_2=R_3=\beta$—hydroxyethyl and $R_4$=H,
    (b) a direct dye wherein $R_1=R_3$=methyl, $R_2=\beta$—hydroxyethyl and $R_4$=H,
    (c) a direct dye wherein $R_1=R_2=R_3=\beta$—hydroxyethyl and $R_4$=H, and
    (d) a direct dye wherein $R_1=R_3$=H, $R_2=\beta$—hydroxyethyl and $R_4$=methyl.

4. The hair dye composition of claim 1 wherein said direct dye is present in an amount ranging from 0.1 to 3 percent by weight based on the total weight of said composition.

5. The hair dye composition of claim 1 wherein said imidazolidinedione is present in an amount ranging from 0.3 to 3 percent by weight based on the total weight of said composition.

6. The hair dye composition of claim 1 wherein said solvent is water or an alcohol, said solvent being present in an amount ranging from 0.5 to 20 percent by weight based on the total weight of said composition.

7. The hair dye composition of claim 6 wherein said solvent is present in an amount ranging from 2 to 10 percent by weight based on the total weight of said composition.

8. The hair dye composition of claim 1 having a pH ranging from 4 to 10.5.

9. A process for dyeing hair comprising applying to said hair a hair-dyeing amount of the composition of claim 1, permitting said hair dye composition to remain in contact with the hair for a period of time ranging from 3 to 60 minutes and rinsing said hair.

* * * * *